United States Patent [19]
Galel et al.

[11] Patent Number: 5,632,734
[45] Date of Patent: May 27, 1997

[54] CATHETER SHAPE CONTROL BY COLLAPSIBLE INNER TUBULAR MEMBER

[75] Inventors: Zev Galel, Los Altos Hills; Cem Kilicci, San Francisco; Henry Bourang, Campbell, all of Calif.

[73] Assignee: Guided Medical Systems, Inc., Mountain View, Calif.

[21] Appl. No.: 541,453

[22] Filed: Oct. 10, 1995

[51] Int. Cl.$^6$ .................................................. A61M 25/00
[52] U.S. Cl. ..................... 604/282; 609/283; 128/772; 607/122; 138/120; 138/DIG. 8
[58] Field of Search .................. 604/49, 52, 53, 604/264, 280–282; 128/657, 772; 607/98–101, 119, 122; 600/16; 138/119, 120, 155, DIG. 8

[56] References Cited

U.S. PATENT DOCUMENTS

| | | | |
|---|---|---|---|
| 4,033,331 | 7/1977 | Guss et al. | 128/2 |
| 4,323,071 | 4/1982 | Simpson et al. | 128/343 |
| 4,432,349 | 2/1984 | Oshiro | 138/120 |
| 4,516,972 | 5/1985 | Samson | 604/282 |
| 4,790,331 | 12/1988 | Okada et al. | 128/772 |
| 4,852,564 | 8/1989 | Sheridan et al. | 138/DIG. 8 |
| 4,873,965 | 10/1989 | Danieli | 138/120 |
| 4,898,577 | 2/1990 | Badger et al. | 604/53 |
| 4,925,445 | 5/1990 | Sakamoto et al. | 128/772 |
| 4,935,017 | 6/1990 | Sylvanowicz | 604/280 |
| 4,960,411 | 10/1990 | Buchbinder | 604/95 |
| 5,030,204 | 7/1991 | Badger et al. | 604/95 |
| 5,098,412 | 3/1992 | Shiu | 604/280 |
| 5,109,830 | 5/1992 | Cho | 128/772 |
| 5,114,414 | 5/1992 | Buchbinder | 604/95 |
| 5,120,323 | 6/1992 | Shockey et al. | 604/282 |
| 5,131,406 | 7/1992 | Kaltenbach | 128/772 |
| 5,203,280 | 4/1993 | Chikama | 138/DIG. 8 |
| 5,211,183 | 5/1993 | Wilson | 128/657 |
| 5,231,989 | 8/1993 | Middleman et al. | 128/657 |
| 5,267,982 | 12/1993 | Sylvanowicz | 604/281 |
| 5,290,229 | 3/1994 | Paskar | 604/95 |
| 5,304,131 | 4/1994 | Paskar | 604/95 |
| 5,308,342 | 5/1994 | Sepetka et al. | 604/282 |
| 5,391,147 | 2/1995 | Imran et al. | 604/95 |
| 5,448,989 | 9/1995 | Heckele | 604/282 |
| 5,496,294 | 3/1996 | Hergenrother et al. | 604/282 |
| 5,549,581 | 8/1996 | Lurie et al. | 604/282 |
| 5,569,218 | 10/1996 | Berg | 604/282 |
| 5,569,221 | 10/1996 | Houser et al. | 604/282 |

*Primary Examiner*—Michael Powell Buiz
*Assistant Examiner*—Chalin Smith
*Attorney, Agent, or Firm*—Townsend and Townsend and Crew LLP

[57] ABSTRACT

A composite catheter is formed by the combination of a catheter body and a tubular member insertable or secured inside the catheter body. The tubular member contains a series of relatively rigid segments alternating with flexible, collapsible segments which permit the rigid segments to effectively stack against one another when the tubular member is compressed axially. The shape that results when the rigid segments are forced together differs from that of the shape memory of the catheter body in certain embodiments of the invention, and changing the tubular member from a relaxed condition to the compressed condition inside the catheter body can therefore cause a change in shape of the catheter body.

15 Claims, 10 Drawing Sheets

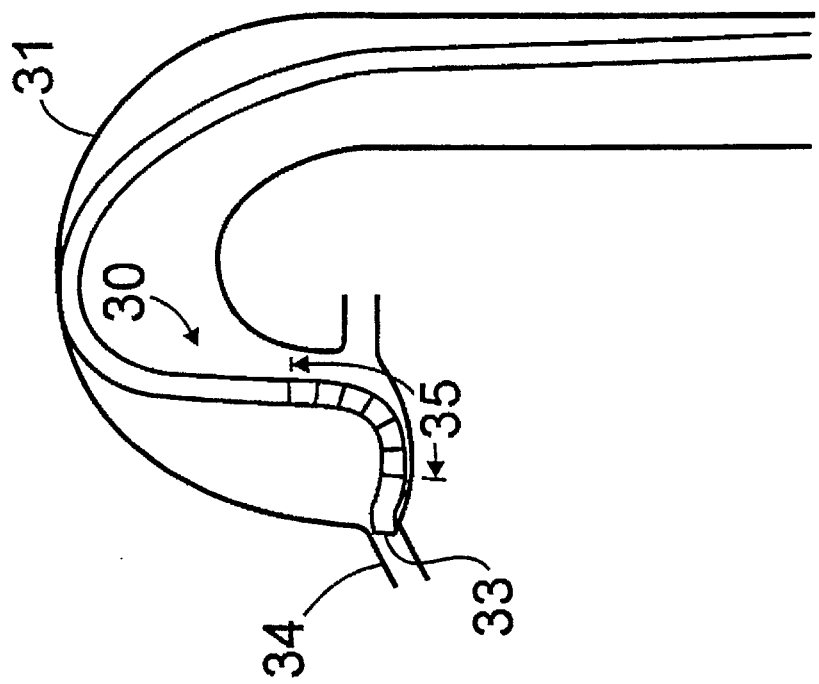
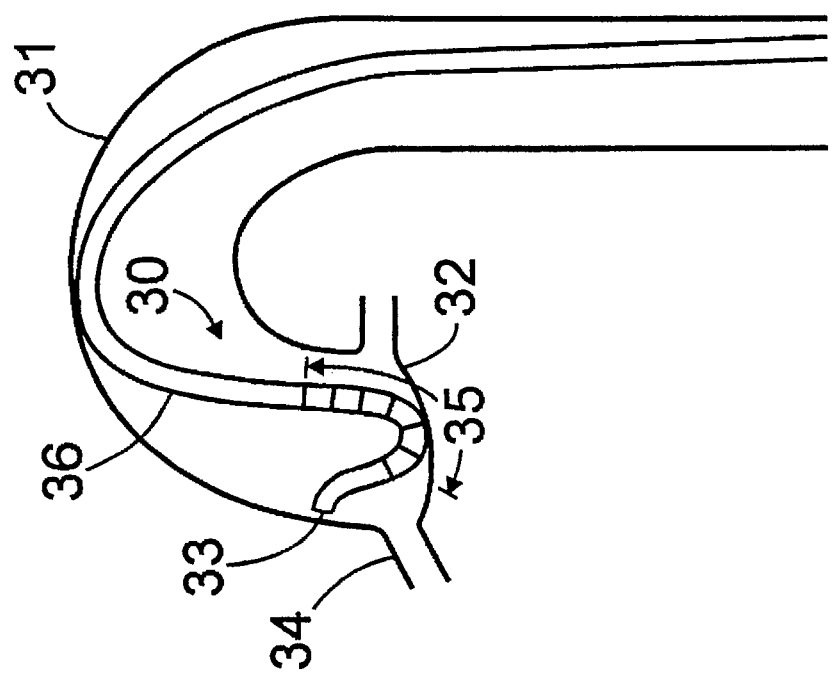

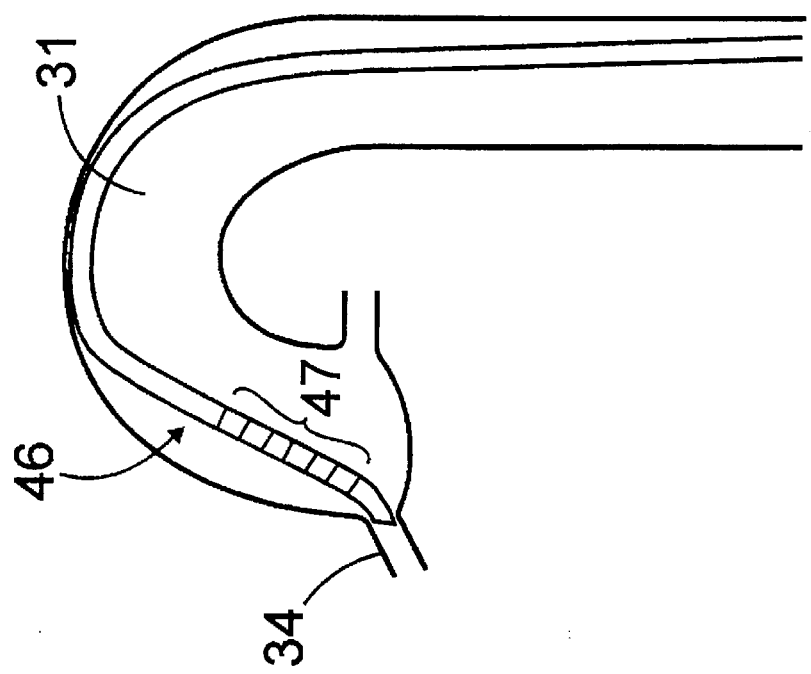
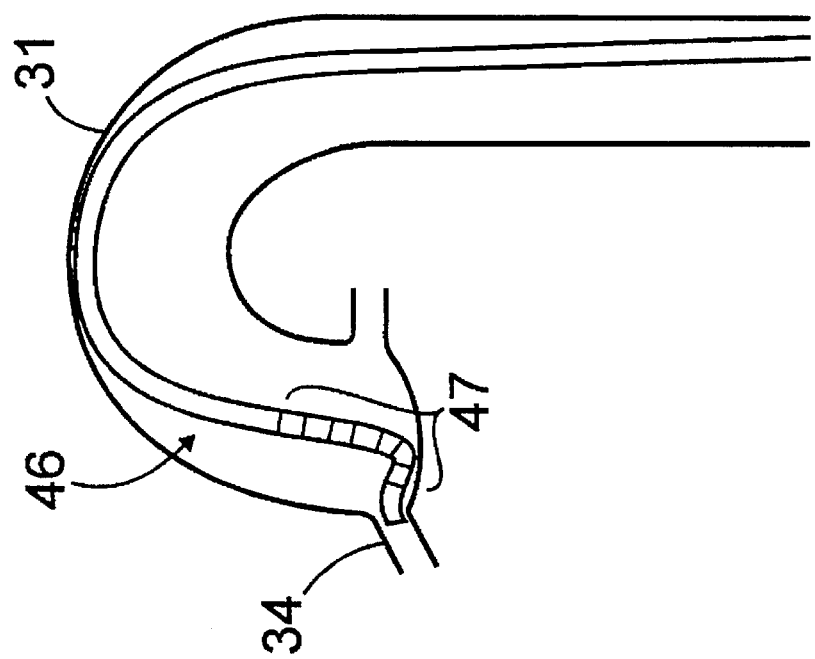

CATHETER SHAPE CONTROL BY COLLAPSIBLE INNER TUBULAR MEMBER

BACKGROUND OF THE INVENTION

This invention resides in the construction and use of catheters for interventional procedures in fields such as cardiology, neuroradiology, urology and gastroenterology.

A major problem in the use of catheters for these procedures lies in the insertion of the catheter through bodily passages to reach the vessel or chamber of interest and the placement of the functional element at the distal tip of the catheter at the site where that element is needed. In some procedures, holding the element at the site while the site moves in response to normal bodily functions such as breathing or a heart beat is also a problem.

Guide catheters are a partial means of solving these problems. Guide catheters are relatively large lumen catheters used to guide smaller diameter catheters such as therapeutic, diagnostic or imaging catheters into bodily passages that are curved or branched. A guide catheter specially designed for a procedure in a coronary artery, for example, is shaped such that when the guide catheter is inserted into the femoral artery and through the aorta of a patient, the curvature of the catheter will place its distal tip inside one of the coronary ostia. Thus, a guide catheter for the right coronary artery is shaped differently than one for the left coronary artery. A guide catheter designed to provide access to a carotid artery is still different in shape. Guide catheters of still other shapes are designed for other bodily passages and regions of interest.

Guide catheters currently available from suppliers occur in a variety of shapes designed for different bodily passages and procedures. Those of skill in the art recognize these different shapes by names such as Judkins Right, Judkins Left, Amplatz Right, Amplatz Left, Bentson, Shepherd Hook, Cobra, Headhunter, Sidewinder, Newton, Sones and others, each formed into a different shape. Most of these different shapes are manufactured in gradations of size and/or curvature to accommodate differences among individual patients.

When a guide catheter is inserted in a patient, its shape is distorted by the connecting passages, such as the aortic arch or the venae cavae. The curves or bends close to the distal end of the catheter retain their shape, however, which is intended to place the opening at the distal end of the guide catheter at the desired location in the vessel or on the vessel wall. Improved control and stabilization of the catheter position is often achieved by anchoring the catheter against an opposing wall, and the ability to do this also depends on the predisposed shape of the catheter.

The dimensions of bodily passages differ from one patient to the next, however, and for proper stabilization and direction of the operating catheter, a guide catheter of the appropriate dimensions must be used. To accommodate this, operating rooms are equipped with a range of sizes of each of the various catheters so that the operator can select the one most suited to the patient, or exchange one already selected for one with a better fit.

Since measurements of these bodily passages cannot be taken prior to insertion of the guide catheter, the physician often relies on visualization devices or techniques incorporated in the catheter body to determine whether the catheter is properly positioned. If the catheter cannot be properly positioned, it must be removed and replaced with one of a different size. This procedure is typically repeated until an acceptable placement is achieved. If this requires many attempts, the cost of the procedure is high due to doctor time and equipment (each catheter is typically disposed of after a single use). Also, the excessive use of contrast media associated with each placement attempt is not desirable. The risk of infection also rises with multiple insertions since the major potential sources of infection are the patient's own skin contaminants and contamination from the operators, both of which are introduced at the insertion site. Still further, multiple insertions increase the risk of trauma to the vessels receiving the catheters.

SUMMARY OF THE INVENTION

The problems noted above as well as others associated with catheter shapes and manipulations are addressed by the present invention. This invention resides in a composite catheter to which a curvature in the distal region can be either imposed, removed, or changed, or whose rigidity can be increased, all by manipulation of the catheter at its proximal end. The manipulation can be done either prior to or after insertion of the catheter into the body. The invention further resides in the shape-modifying component of the composite catheter that permits the manipulation to be performed. This invention is applicable to catheters in general, including but not limited to guide catheters.

The composite catheter includes a catheter body and a tubular member either residing inside the catheter body or insertable into it, but in either case movable within the catheter body. The distal end of the tubular member contains a series of relatively rigid segments alternating with segments that are collapsible along the axis of the tubular member. The tubular member can thus be manipulated between a compressed configuration in which the rigid segments are stacked to form a self-supporting tube of fixed curvature or straightness, and an extended configuration in which the rigid segments are spaced apart sufficiently to allow variations in the directions of individual segments. The rigid segments themselves can be straight, as sections of a straight cylinder, or curved, as sections of a torus (the surface generated by a circle rotating about but not intersecting an axis in its own plane, i.e., a doughnut shape).

The catheter body is flexible relative to the tubular member, and will preferably have a shape memory which it will assume when not influenced by the tubular member or its relatively rigid segments. When the tubular member is inside the catheter body and compressed to collapse the connecting segments, the catheter body will assume a curvature (or straightness) similar to that of the stacked rigid segments of the tubular member. When the compression is released, the catheter body will revert to its shape memory or to an intermediate shape resulting from any residual influence of the tubular member still retained inside. Compression of the segments in the tubular member can therefore either increase the curvature of the catheter body (i.e., shorten the radius of curvature) or decrease it (lengthen the radius of curvature), depending on the shape memory of the catheter body and the shapes of the segments.

The distal segment of the tubular member can be fixed inside the catheter body at a location that will result in the proximal end of the tubular member residing outside the catheter body. Rigidification or relaxation can then be achieved by pushing or pulling on the proximal end of the tubular member. Alternatively, the tubular member can be separate from and not joined to the catheter body. Rigidification and relaxation of the catheter with these non-joined components can be achieved outside the patient's body by inserting the tubular member into the catheter body and manually squeezing or pinching the catheter body around the distal tip of the tubular member to anchor the distal tip while the proximal end of the tubular member is moved in or out.

When the composite of the catheter body and tubular member serves as a guide catheter, the tubular member lumen will accommodate functional catheters as do the lumens of conventional guide catheters.

One of the many uses of the composite catheter of this invention is as a guide catheter for electrophysiology procedures such as the mapping and ablation procedure referred to above. These procedures require that the guide catheter be curved sufficiently in the direction of the wall of the heart chamber that the tip of the ablation catheter presses against the locus of the arrhythmia. The guide catheter however must be sufficiently straight to be directed through the valves into the appropriate chamber. After the guide catheter has been fully inserted, the tubular member can be manipulated to change the shape of the guide catheter from straight to curved. Depending on the shape memory of the catheter body and the shapes of the rigid segments of the tubular member, this change may be effected either by relaxing the tubular member or by compressing it.

These and other features, fields of use and advantages of the invention will become evident from the following description.

BRIEF DESCRIPTION OF THE DRAWINGS

FIG. 6 is a cross section of a human aorta with a composite catheter of this invention inserted through the aorta to the right coronary artery.

FIG. 7 is the same view as FIG. 6, with the composite catheter in a configuration resulting from compression of the tubular member.

FIG. 10 is a cross section of a human aorta with a third composite catheter of this invention inserted through the aorta to the right coronary artery.

FIG. 11 is the same view as FIG. 10, with the composite catheter in a configuration resulting from compression of the tubular member.

DETAILED DESCRIPTION OF THE INVENTION AND PREFERRED EMBODIMENTS

The concepts of this invention can be embodied in catheter constructions varying widely in shape, size and configuration, and thereby useful for a variety of bodily passages and types of clinical procedures. For a better understanding of the invention, this section of the specification describes several specific constructions in detail, each of which serves as an example of the implementation of the concepts of this invention.

Figure 1:
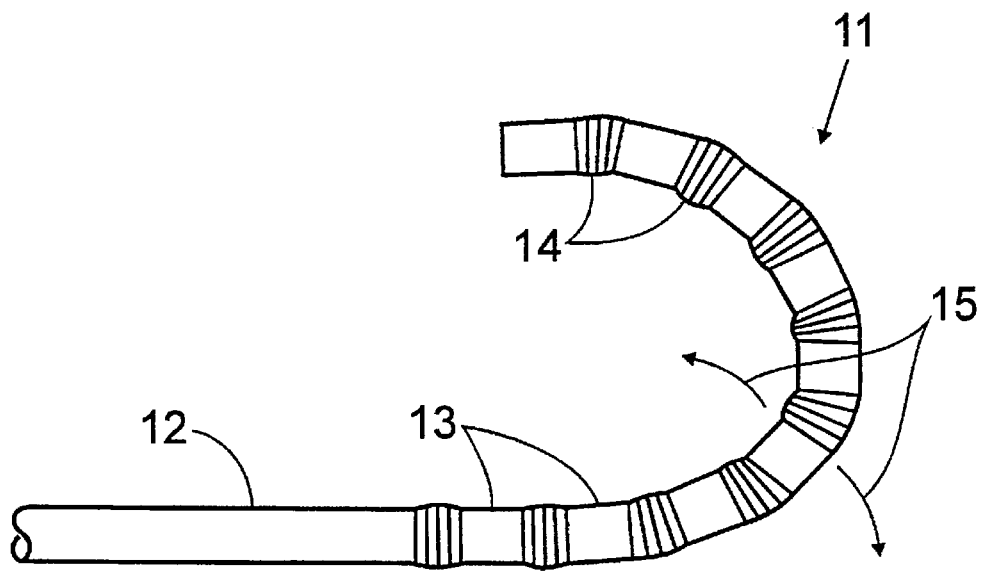
FIG. 1 is a side view of a tubular member in accordance with this invention, in a relaxed state.
Figure 2:
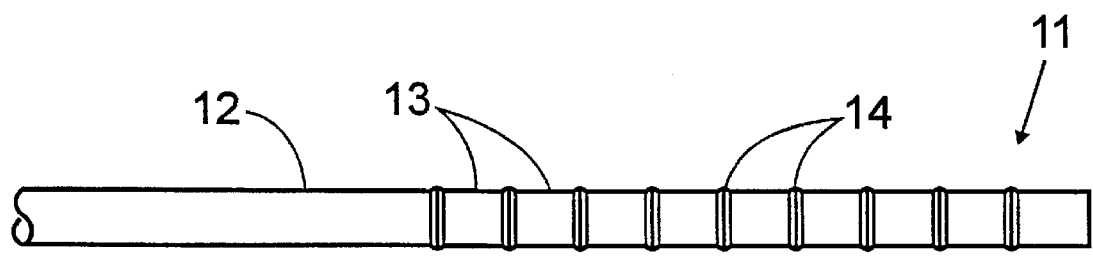
FIG. 2 is a side view of the tubular member of FIG. 1 in the compressed state.

FIGS. 1 and 2 illustrate a single tubular member 11 prior to insertion in, or fixation to, a catheter body. The distal region of the tubular member is shown in both Figures, in a partially extended condition in FIG. 1 and in a compressed condition in FIG. 2. The tubular member is made up of a shaft 12 and a series of short cylindrical segments 13 separated by connecting segments 14. The shaft 12 and cylindrical segments 13 are hollow cylinders or cylindrical sections, and are relatively rigid, with sufficient rigidity to resist axial collapse under an axially directed force or bending under a lateral torque. The connecting segments 14 are also cylindrical segments but are flexible, collapsing under an axial force or bending under a lateral torque.

When the tubular member 11 is compressed as in FIG. 2, the rigid cylindrical segments 13 are pushed together, causing the connecting segments 14 to buckle and bunch up as shown. The stacked rigid segments 13 form a straight length of relatively rigid tubing. When the tubular member 11 is relaxed, permitting the connecting segments to spread, the distal region of the tubular member 11 loses its rigidity and can bend as indicated by the arrows 15. The tubular member is shown curved to one side to indicate its flexibility.

Figure 3:
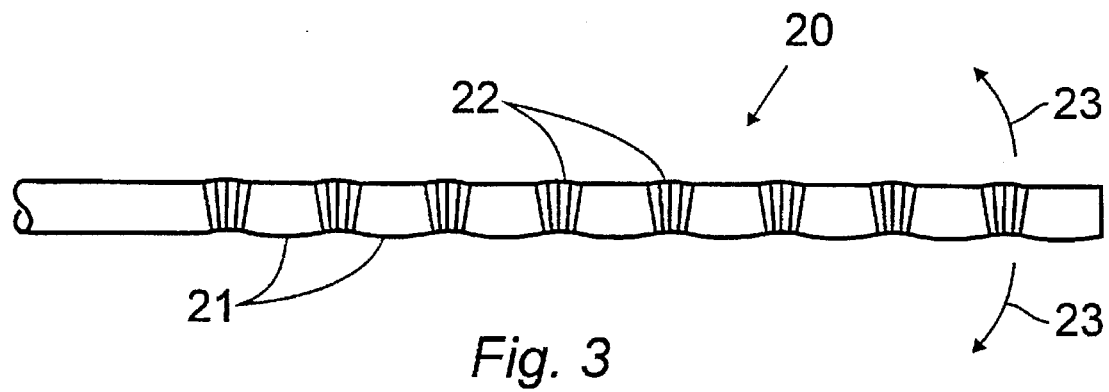
FIG. 3 is a side view of a second tubular member of this invention, in a relaxed state.
Figure 4:
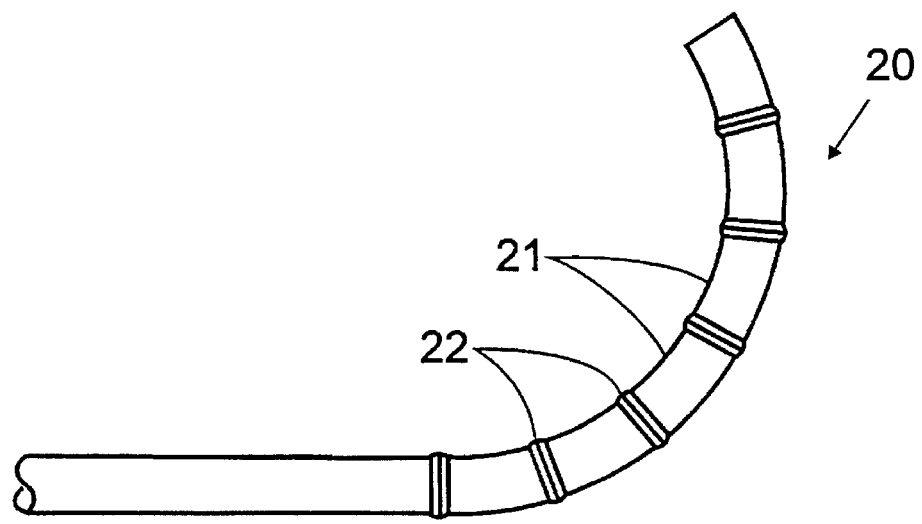
FIG. 4 is a side view of the tubular member of FIG. 3 in the compressed state.

FIGS. 3 and 4 illustrate a tubular member 20 which forms a curve when compressed. The rigid segments 21 are sections of a torus, and when stacked against each other, compressing the flexible connecting sections 22 in between, they form a curved tube, as shown in FIG. 4 which shows the tubular member compressed. When not compressed, the tubular member is flexible, and can be straight as shown in FIG. 3, curved to a greater or lesser degree than shown in FIG. 4, or in a different direction. The flexibility in the non-compressed condition is indicated by the arrows 23 in FIG. 3.

Figure 5:
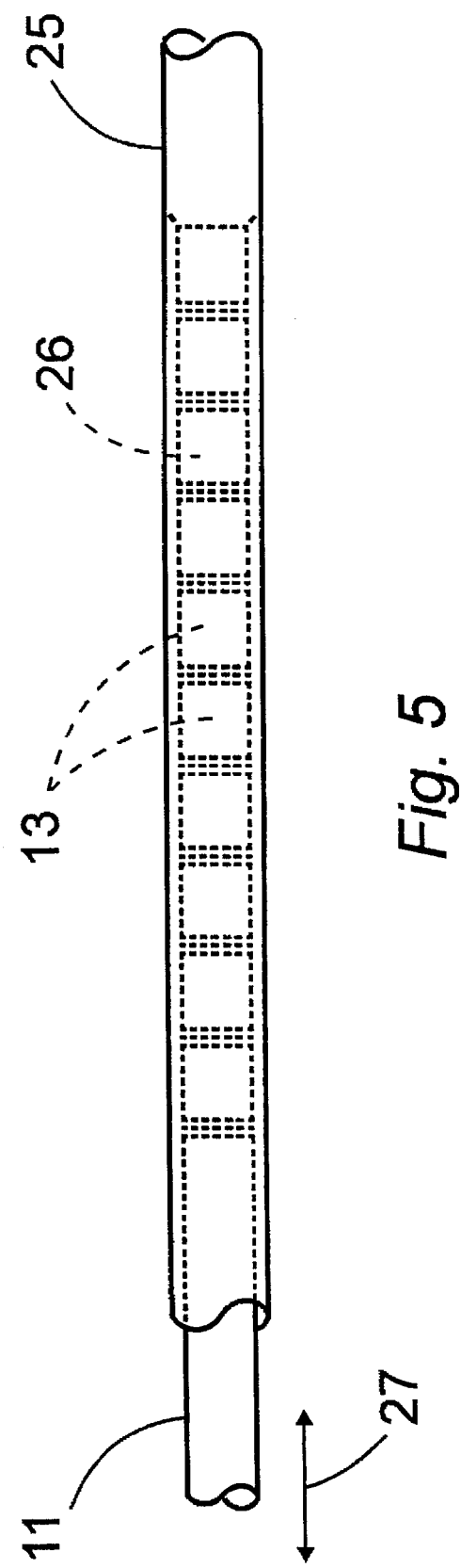
FIG. 5 is a side view of a section of a composite catheter in accordance with this invention, with a portion of the tubular member shown in dashed lines.

The tubular member 11 of FIGS. 1 and 2 is shown inside a catheter body 25 in FIG. 5. The tubular member 11, much of which is shown in dashed lines, is shown in the compressed condition in this drawing, causing the rigid segments 13 to align into a straight tube, and thereby cause the catheter body 21 to straighten as well. The rigid segment at the distal end 26 is bonded to the inside surface of the catheter body 21. The remaining rigid segments can then be forced against each other or separated from each other by simply moving the tubular member in the direction indicated by the arrows 27.

FIGS. 6 and 7 illustrate a catheter of the invention having a shape of the Amplatz Right type 30. The catheter is inserted in an aorta, passing through the aortic arch 31 to the aortic root 32, in an attempt to place the distal end 33 of the catheter inside the entry to the right coronary artery 34. The catheter is a composite of the catheter body and tubular member as discussed above.

In FIG. 6, the tubular member is relaxed, and the section 35 of the catheter body in which the separated rigid sections of the tubular member reside is curved to follow the shape memory of the catheter body 36, since the portion of the tubular member formed by the separated tubular sections is flexible. The distal tip 33 is not properly placed, however, being too high to enter the coronary artery 34. This is corrected in FIG. 7 where the section 35 of the catheter body in which the separated rigid sections of the tubular member reside is shortened and partially straightened by forcing the rigid sections against each other. This is done by forcing the tubular member inward from the proximal end while its distal end is affixed to the inside wall of the catheter body. The result of the change in shape is a more gentle curve in the distal region of the catheter body, aligning the distal tip 33 with the artery 34.

Figure 9:
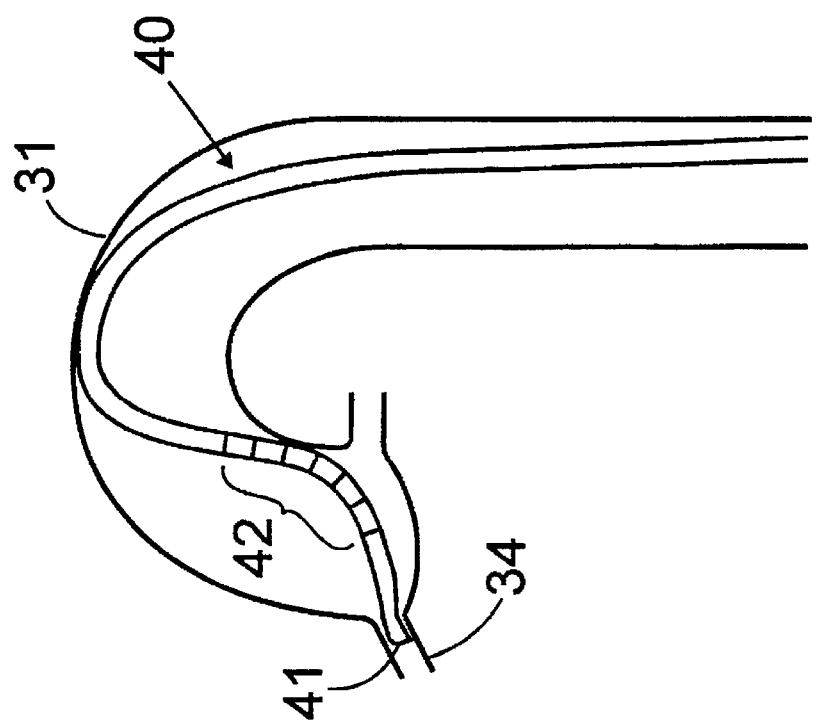
FIG. 9 is the same view as FIG. 8, with the composite catheter in a configuration resulting from compression of the tubular member.
Figure 8:
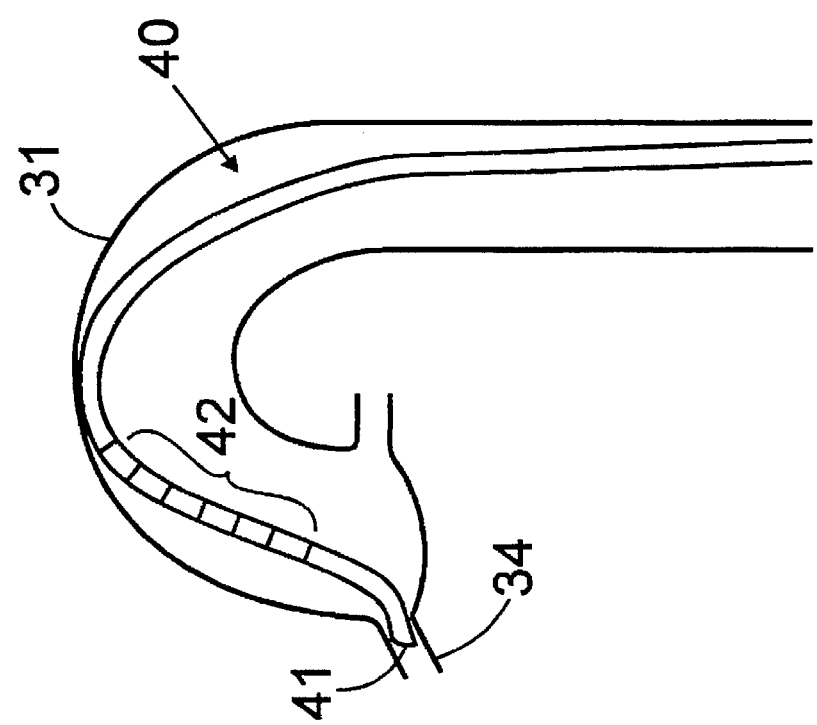
FIG. 8 is a cross section of a human aorta with a second composite catheter of this invention inserted through the aorta to the right coronary artery.

FIGS. 8 and 9 illustrate a catheter of the Judkins Right type 40. The catheter passes through the aortic arch 31, and its distal tip 41 enters the right coronary artery 34. Like the catheter of FIGS. 6 and 7, this catheter is a composite of the catheter body and tubular member.

In FIG. 8, the tubular member is relaxed and its rigid segments separated. The individual rigid segments are slightly curved, as in FIGS. 3 and 4, while the shape memory of the catheter body in the vicinity of these segments is straight. Thus, with the rigid segments separated, the shape of the section 42 of the catheter body immediately adjacent to these rigid segments is approximately straight since it is governed by the shape memory. The result is that, while the distal tip 41 is properly placed inside the right coronary artery 34, the remainder of the composite catheter is not anchored anywhere other than at the top of the aortic arch 31.

This is corrected in FIG. 9 in the same manner as in FIG. 7, by forcing the tubular member inward from the proximal end, its distal end being affixed to a site inside the catheter body. This forces the rigid segments against each other to form a curve which is relatively rigid and overcomes the straightness of the shape memory. The catheter is now anchored against the wall of the aortic root opposite the right coronary artery.

FIGS. 10 and 11 illustrate a composite catheter 46 that has a Judkins Right shape when the tubular member is compressed and an Amplatz Right shape when the tubular member is relaxed. The individual rigid segments of the tubular member are straight, unlike those in the composite catheter of FIGS. 8 and 9. Thus, when the tubular member is compressed, as it is in FIG. 11, the rigid segments form a substantially straight line like the corresponding portion of the conventional Judkins shape. The section 47 of the catheter body where the rigid segments of the tubular member reside has a curved shape memory, which it assumes in the relaxed configuration of FIG. 10, but which is changed into the relatively straight Judkins shape in FIG. 11.

Figure 12:
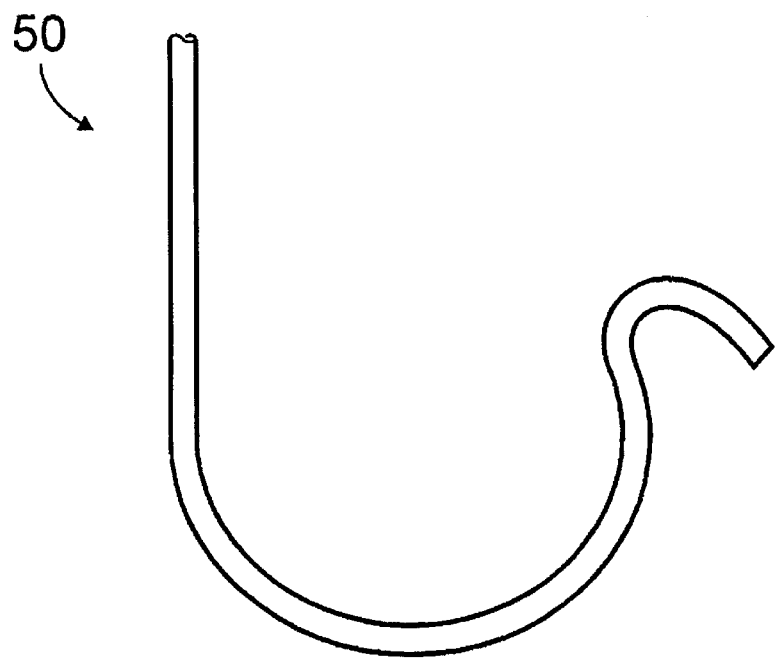
FIG. 12 is a side view of a catheter body in accordance with this invention, without a tubular member inside.
Figure 13:
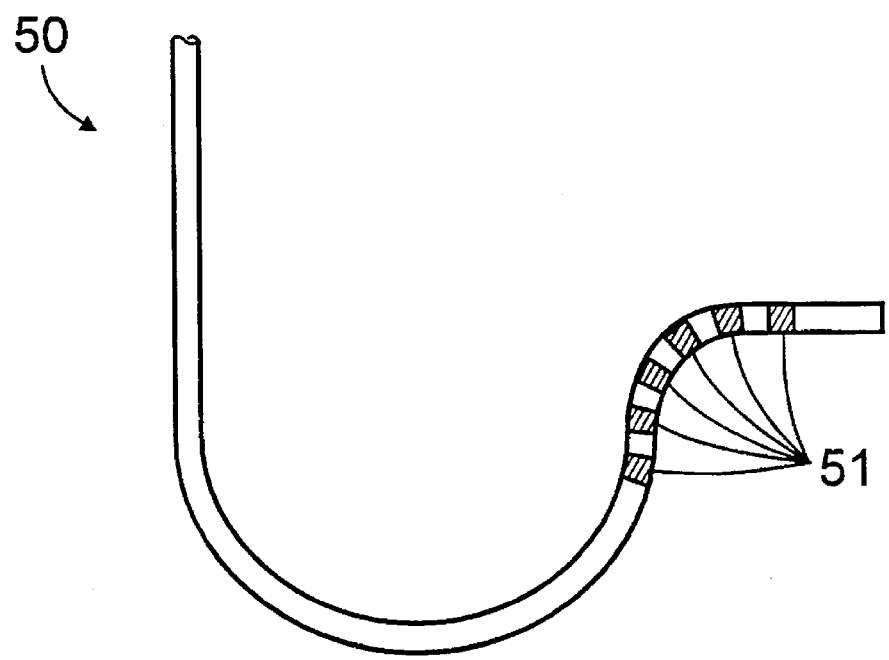
FIG. 13 is the same view as FIG. 12, except that a tubular member has been placed inside the catheter body and held in a relaxed or extended condition.
Figure 14:
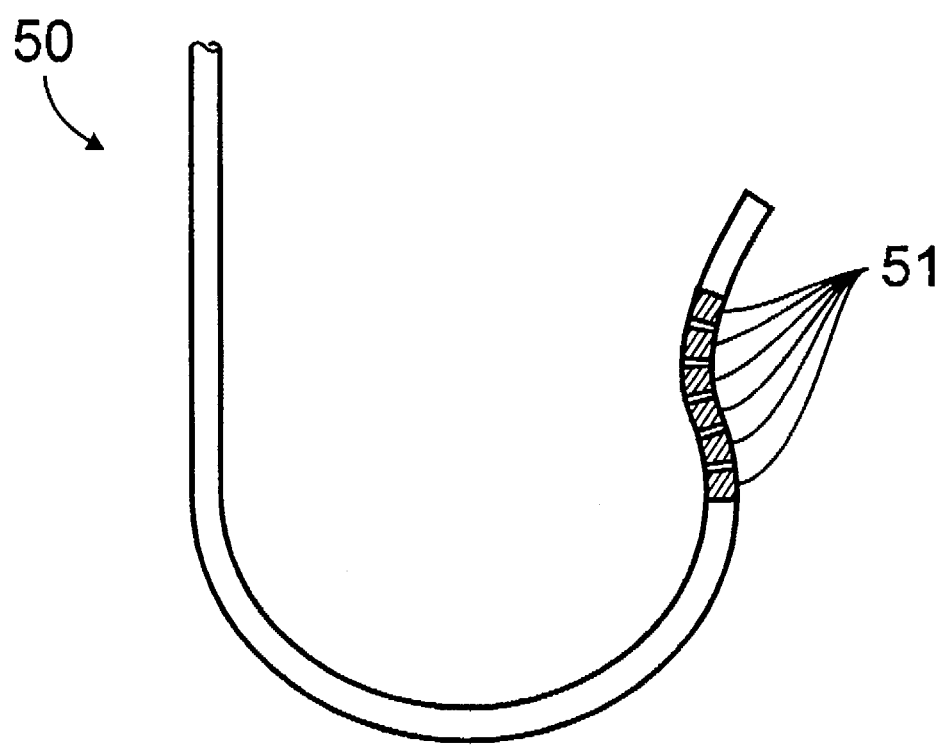
FIG. 14 is the same view as FIG. 13, except that the tubular member has been compressed.

Even when the rigid segments are separated (and the connecting segments fully extended), the tubular member can force the catheter body to deviate from its shape memory. The degree of deviation caused by an extended tubular member will vary depending on the lengths of the rigid segments and the connecting segments, longer rigid segments and shorter connecting segments producing greater deviation. The composite catheter can thus have three distinct shapes or degrees of curvature —one with the tubular member removed entirely from the catheter body, a second with the tubular member inserted in the catheter body but the connecting segments fully extended, and a third with the tubular member inserted and the connecting segments collapsed so that the rigid segments are compressed against each other. An example of a composite catheter 50 with this characteristic is shown in FIGS. 12 (catheter body alone), 13 (catheter body with relaxed tubular member) and 14 (catheter body with compressed tubular member). The rigid segments 51 of the tubular member (shown through the catheter body in these figures), are straight while the shape memory of the catheter body is curved. Accordingly, the tubular member reduces the curvature of the catheter body to successive degrees, as represented by the Figures in the order shown. The opposite effect is readily achieved by a catheter body with relatively straight shape memory and a tubular member with curved rigid segments.

Figure 15:
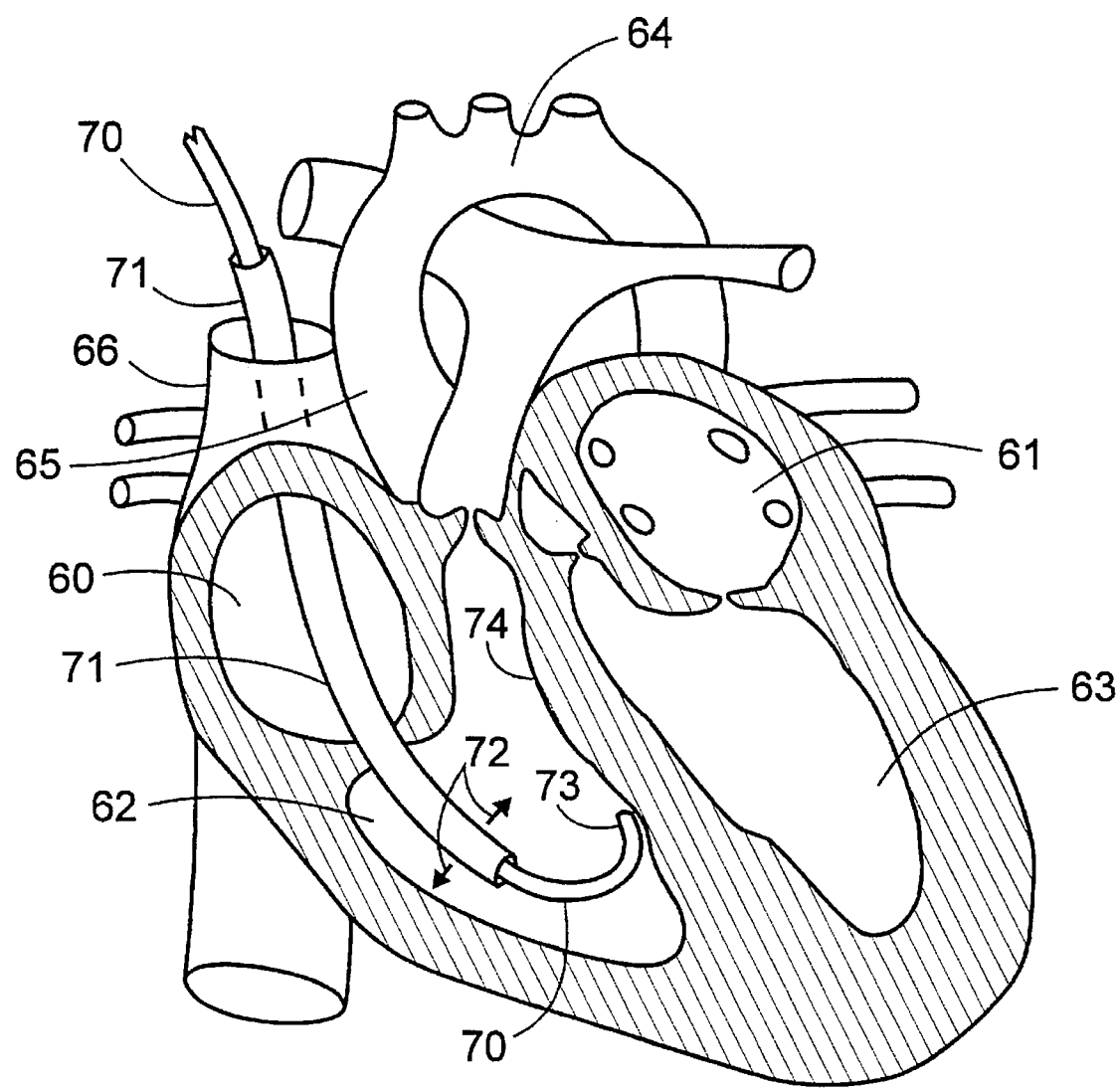
FIG. 15 is aから view of a human heart in cross section, with a composite catheter in accordance with this invention placed inside the right ventricle and a mapping and ablation catheter passing through the guide catheter.
Figure 16:
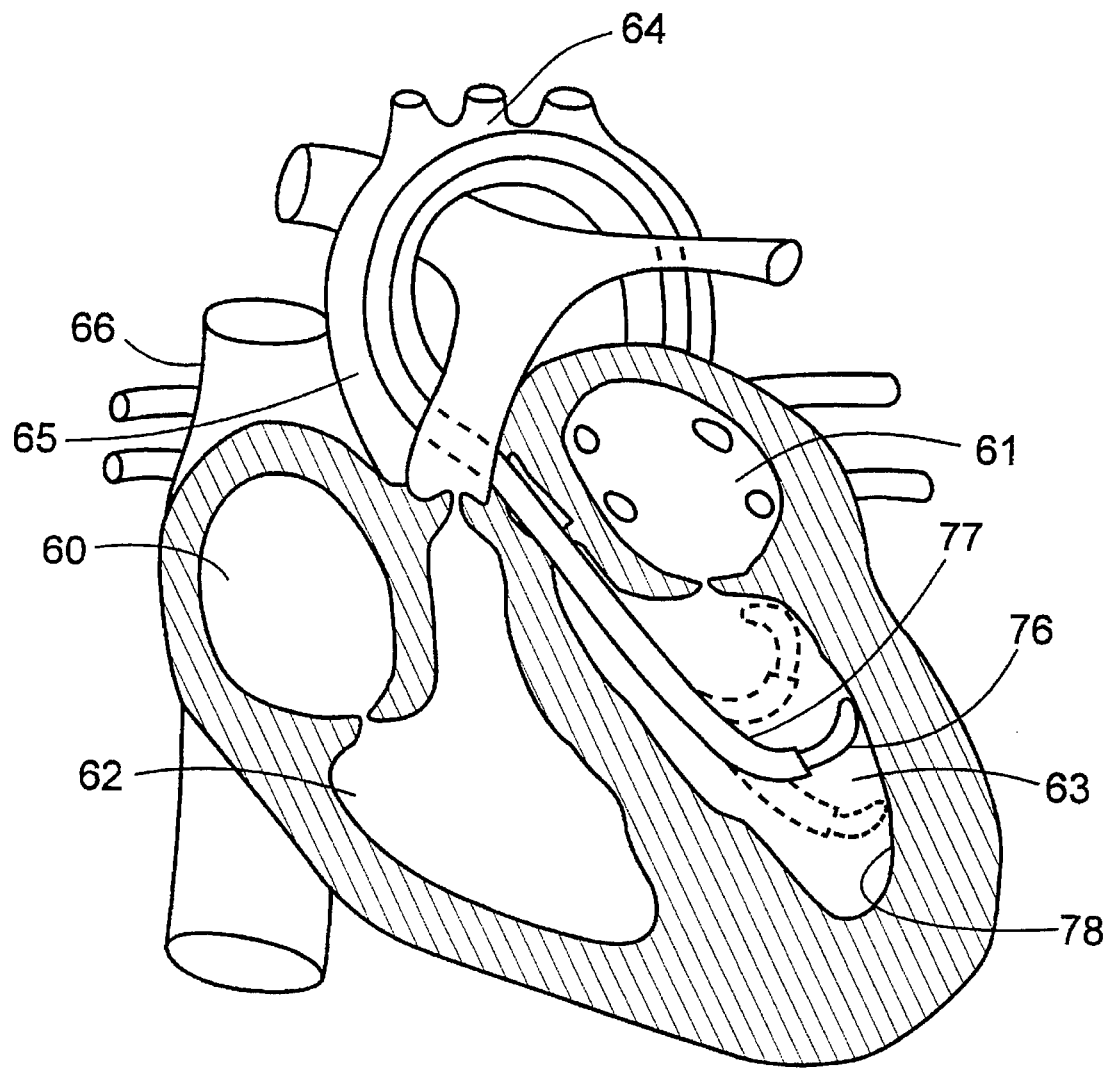
FIG. 16 is a front view of a human heart in cross section, with a composite catheter in accordance with this invention placed inside the left ventricle and a mapping and ablation catheter passing through the guide catheter.

The application of the invention to electrophysiology procedures is illustrated in FIGS. 15 and 16. Each of these Figures shows a cross section of the human heart, showing the right atrium 60, left atrium 61, right ventricle 62, left ventricle 63, aortic arch 64, ascending aorta 65 and superior vena cava 66.

FIG. 15 illustrates mapping and ablation in the right ventricle 62 by the use of a mapping and ablation catheter 70 directed to the appropriate chamber wall by a composite guide catheter 71 in accordance with this invention. Manipulation of the tubular member (not shown) inside the guide catheter permits the operator to move the guide catheter in the direction of the arrows 72, to adjust the pressure of the ablation tip 73 against the chamber wall 74.

FIG. 16 illustrates mapping and ablation in the left ventricle 63, again by the use of a mapping and ablation catheter 76 directed by a composite guide catheter 77 in accordance with this invention. Manipulation of the tubular member (not shown) permits the operator to adjust the position of the guide catheter in the directions indicated by the dashed lines to reach a range of locations on the chamber wall 78 and to apply sufficient pressure to maintain contact.

In either case, once the ablation tip is in position and appropriate pressure is established, the tip is actuated and the procedure is performed.

The following considerations are applicable to all composite catheters of this invention, regardless of their shapes or the type or degree of change achieved by manipulation of the tubular member.

The rigid sections in any single tubular member can be identical in all respects or they can vary such as by differing in length, curvature or rigidity. Specialized shapes of highly controlled curvature and specialized shape changes can be obtained by a appropriate combination of rigid sections of differing dimensions or construction. The lengths of the collapsible connecting sections in a single tubular member can likewise vary to achieve a similar effect.

The rigid sections are preferably rings ranging from about 0.1 cm to about 1.0 cm in length, and most preferably about 0.2 cm to about 0.3 cm. The collapsible connecting segments are generally of a similar size.

The rigid segments may be formed of metals or metal alloys, although hard plastics or composites can also be used. The connecting elements may be thin-wall Teflon tubing, or any other compressible or collapsible material. The number of rigid segments will depend on the type and degree of curvature change, but in general, there will be at least four such segments, preferably ten to thirty.

The uncurved length of the catheter body will generally range from about 50 cm to about 150 cm, preferably from about 90 cm to about 120 cm. The diameter of the catheter body will most often be in the range of about 4 French (F, where 1 F=0.33 mm) to about 12 F, and preferably from about 6 F to about 11 F. The catheter body will have a lumen with a diameter of from about 1.75 mm to about 3.0 mm, preferably from about 2.0 mm to about 2.75 mm. The tubular member will be small enough to fit within the lumen of the catheter body with a sufficiently loose fit to be moved longitudinally inside the lumen, but large enough so that the lumen of the tubular member itself can accommodate a working catheter, or two or more if necessary.

The shape memory of the catheter body when not under the influence of the tubular member may be inherent in the catheter body itself, imposed by molding, tempering, or alloying techniques or other methods known to those skilled in the art. Alternatively, the shape memory may be imparted and maintained by one or more spring rods (not shown in the drawings) embedded in the wall of the catheter body. The spring rods will be straight or curved as needed, and will be resilient enough that their shapes will be modified by the rigid segments of the tubular member yet capable of resuming the curvature when the rigid segments are removed.

Manipulation of the tubular member is performed at the proximal end of the catheter, outside the patient's body. Manipulation is readily performed by hand, with the operator assisted by visualization of the distal tip of the catheter. Visualization may be achieved by conventional means. Fluoroscopy, a common visualization technique for catheters, is one example. The movement and securement of the tubular member relative to the catheter body can be achieved at the proximal end by simple mechanical devices. Examples are a threaded knob, a ratchet-type mechanism, or various kinds of toothed or locking mechanisms which can be manipulated by hand. Other examples will be readily apparent to those skilled in the art. One specific example is a toothed track on a stationary member to which the catheter body is mounted, and a spring-loaded catch on a mobile member to which the tubular member is mounted, the catch mounted through a pivot to a toothed wheel. When the wheel is pushed by the user's thumb to engage the track, the catch is lifted away from engagement with the track. Turning of the wheel while pressing it against the track by the user's thumb moves the mobile member relative to the stationary member, and release of the wheel causes the catch to engage the track, locking the members relative to each other. Many other mechanisms with a similar ease of manipulation can be substituted.

The foregoing is offered primarily for purposes of illustration. It will be readily apparent to those skilled in the art that the components, their shapes, materials of construction, and methods of use as described herein may be further modified or substituted in various ways without departing from the spirit and scope of the invention.

We claim:

1. A composite catheter comprising:
   a catheter body of flexible construction; and
   a tubular member having a longitudinal axis and sized to be received inside a lumen of said catheter body in a manner permitting movement of said tubular member relative to said catheter body, said tubular member comprising a plurality of shape-limiting segments each of which is substantially non-collapsible axially, adjacent pairs of said shape-limiting segments joined by connecting segments that are axially collapsible and that thereby permit said tubular member to vary between a compressed configuration in which said connecting segments are collapsed and an extended configuration in which said connecting segments are not collapsed.

2. A composite catheter in accordance with claim 1 in which said catheter body is resilient and has a shape memory, and said compressed configuration of said tubular member differs in shape from said shape memory.

3. A composite catheter in accordance with claim 2 in which said compressed configuration is more curved than said shape memory.

4. A composite catheter in accordance with claim 2 in which said shape memory includes a curvature, and said compressed configuration is less curved than said shape memory.

5. A composite catheter in accordance with claim 1 in which said shape-limiting segments are comprised of rings.

6. A composite catheter in accordance with claim 5 in which said rings are of equal radius and equal length.

7. A composite catheter in accordance with claim 5 in which said rings are of individually from about 0.1 cm to about 1.0 cm in length.

8. A composite catheter in accordance with claim 5 in which said rings are of individually from about 0.1 cm to about 1.0 cm in length, and said connecting segments are from about 0.1 cm to about 1.0 cm in length.

9. A composite catheter in accordance with claim 5 in which said rings are from ten to thirty in number.

10. A composite catheter in accordance with claim 1 in which said tubular member has a distal end, and said shape-limiting segments include a distal shape-limiting segment closest to said distal end and bonded to said catheter body.

11. A tubular member for insertion inside a catheter as a means of modifying the shape of said catheter, said tubular member comprising a plurality of shape-limiting segments each of which is substantially non-collapsible axially, adjacent pairs of said shape-limiting segments being joined by connecting segments that are axially collapsible and that thereby permit said tubular member to vary between a compressed configuration in which said connecting segments are collapsed and an extended configuration in which said connecting segments are not collapsed.

12. A tubular member in accordance with claim 11 in which said shape-limiting segments are comprised of rings.

13. A tubular member in accordance with claim 12 in which said rings are each sections of a straight cylinder.

14. A tubular member in accordance with claim 12 in which said rings are each sections of a torus.

15. A method for mapping cardiac tissue in a heart chamber to determine the locus of an arrhythmia and ablating cardiac tissue at said locus, comprising:
   (a) inserting a guide catheter into said heart chamber, said guide catheter comprising
      (i) a catheter body of resilient construction with a shape memory; and
      (ii) a tubular member disposed inside a lumen of said catheter body in a manner permitting movement of said tubular member relative to said catheter body, said tubular member comprising a plurality of shape-limiting segments each of which is substantially non-collapsible axially, adjacent pairs of said shape-limiting segments joined by connecting segments that are axially collapsible and that thereby permit said tubular member to vary between a compressed configuration in which said connecting segments are collapsed and an extended configuration in which said connecting segments are not collapsed;

(b) inserting a mapping and ablation catheter containing an ablation element in a distal region thereof through said tubular member to place said element inside said heart chamber;

(c) adjusting said guide catheter by adjusting said tubular member between said compressed and extended configurations to place said element in contact with said locus and maintain said contact pressure of said element against said locus; and (d) actuating said element while said contact is thus maintained.

* * * * *